(12) United States Patent
Stroup

(10) Patent No.: US 10,299,993 B2
(45) Date of Patent: May 28, 2019

(54) VALVE ASSEMBLY AND METHODS OF USE

(71) Applicant: Infusion Innovations, Inc., La Jolla, CA (US)

(72) Inventor: David Stroup, La Jolla, CA (US)

(73) Assignee: Infusion Innovations, Inc., La Jolla, CA (US)

( * ) Notice: Subject to any disclaimer, the term of this patent is extended or adjusted under 35 U.S.C. 154(b) by 0 days.

(21) Appl. No.: 15/532,563

(22) PCT Filed: Jul. 8, 2016

(86) PCT No.: PCT/US2016/041510
§ 371 (c)(1),
(2) Date: Jun. 2, 2017

(87) PCT Pub. No.: WO2017/008012
PCT Pub. Date: Jan. 12, 2017

(65) Prior Publication Data
US 2018/0000695 A1 Jan. 4, 2018

Related U.S. Application Data

(60) Provisional application No. 62/328,375, filed on Apr. 27, 2016, provisional application No. 62/190,108, filed on Jul. 8, 2015.

(51) Int. Cl.
*A61J 15/00* (2006.01)
*A61M 39/24* (2006.01)
(Continued)

(52) U.S. Cl.
CPC ....... *A61J 15/0076* (2015.05); *A61J 15/0026* (2013.01); *A61J 15/0088* (2015.05);
(Continued)

(58) Field of Classification Search
CPC ............ A61J 15/0026; A61M 5/16804; A61M 5/16881; A61M 5/16813;
(Continued)

(56) References Cited

U.S. PATENT DOCUMENTS

| 3,931,992 A | 1/1976 | Coel |
| 4,694,856 A | 9/1987 | Leibinsohn |

(Continued)

FOREIGN PATENT DOCUMENTS

| CA | 2808186 A1 | 8/2009 |
| EP | 1946792 A1 | 7/2008 |

(Continued)

OTHER PUBLICATIONS

PCT/US2016/041510 International Search Report dated Dec. 2, 2016.
(Continued)

*Primary Examiner* — Kami A Bosworth
*Assistant Examiner* — Alexandra Lalonde
(74) *Attorney, Agent, or Firm* — Wagenknecht IP Law Group PC

(57) ABSTRACT

A valve assembly including a housing having a base and an outer shell, which forms a proximal cavity and a distal cavity joined by a canal; an inner housing configured for longitudinal movement within the distal cavity; a seal positioned within the distal cavity that together with the longitudinal movement of the inner housing regulates the flow of fluid through the valve assembly; and one or more selected from the group consisting of the base notched with one or more notches and the inner housing having one or more through slots aligned to permit access to the one or more notches, the seal being a reversibly deformable sealing pin, and a torque
(Continued)

limiter mechanism configured to resist the longitudinal movement of the inner housing distally until a sufficient radial force is applied.

20 Claims, 10 Drawing Sheets

(51) Int. Cl.
| | |
|---|---|
| *A61M 39/26* | (2006.01) |
| *A61M 5/142* | (2006.01) |
| *A61M 5/168* | (2006.01) |
| *A61M 5/172* | (2006.01) |
| *A61M 5/36* | (2006.01) |
| *F04B 43/12* | (2006.01) |
| *A61M 39/10* | (2006.01) |

(52) U.S. Cl.
CPC .... *A61M 5/14228* (2013.01); *A61M 5/14232* (2013.01); *A61M 5/168* (2013.01); *A61M 5/16804* (2013.01); *A61M 5/172* (2013.01); *A61M 5/365* (2013.01); *A61M 39/24* (2013.01); *A61M 39/26* (2013.01); *F04B 43/12* (2013.01); *A61J 2200/70* (2013.01); *A61M 2039/1033* (2013.01); *A61M 2039/2433* (2013.01); *A61M 2039/263* (2013.01); *A61M 2205/14* (2013.01); *A61M 2205/3334* (2013.01); *A61M 2205/3375* (2013.01); *A61M 2205/6036* (2013.01)

(58) Field of Classification Search
CPC .... A61M 2039/263; A61M 2039/2433; A61M 2039/1061; A61M 2039/1033; A61M 2039/242; A61M 2039/1016; A61M 2039/267; A61M 2039/268; A61M 2039/1072; A61M 2039/2426; A61M 2039/244; A61M 2039/2453; A61M 2039/1038; A61M 2039/1066; A61M 2039/266
See application file for complete search history.

(56) References Cited

U.S. PATENT DOCUMENTS

| | | | |
|---|---|---|---|
| 5,242,393 A | 9/1993 | Brimhall et al. | |
| 5,255,734 A | 10/1993 | Leonard et al. | |
| 5,755,269 A | 5/1998 | Venooker et al. | |
| 6,063,062 A | 5/2000 | Paradis | |
| 6,168,137 B1 | 1/2001 | Paradis | |
| 6,364,869 B1 | 4/2002 | Bonaldo | |
| 6,745,998 B2 | 6/2004 | Doyle | |
| 7,815,614 B2 | 10/2010 | Fangrow, Jr. | |
| 8,603,047 B2 | 12/2013 | Stroup | |
| 8,647,310 B2 | 2/2014 | Fangrow, Jr. et al. | |
| 2002/0133124 A1 | 9/2002 | Leinsing et al. | |
| 2003/0199835 A1 | 10/2003 | Leinsing et al. | |
| 2004/0172006 A1 | 9/2004 | Bonaldo | |
| 2005/0087715 A1* | 4/2005 | Doyle | A61M 39/045 251/149.1 |
| 2005/0090805 A1 | 4/2005 | Shaw et al. | |
| 2006/0142735 A1* | 6/2006 | Whitley | A61M 39/1011 604/537 |
| 2007/0017583 A1 | 1/2007 | Fangrow, Jr. | |
| 2007/0088293 A1 | 4/2007 | Fangrow, Jr. | |
| 2007/0120083 A1 | 5/2007 | Simpson et al. | |
| 2008/0183155 A1 | 7/2008 | Funamura et al. | |
| 2011/0015580 A1 | 1/2011 | Stroup | |
| 2011/0276035 A1 | 11/2011 | Fangrow, Jr. | |
| 2012/0065626 A1 | 3/2012 | Naftalovitz et al. | |
| 2012/0116355 A1* | 5/2012 | Heinz | A61M 5/347 604/535 |
| 2012/0157914 A1* | 6/2012 | Stroup | A61M 39/26 604/68 |
| 2012/0277688 A1 | 11/2012 | Rogier | |
| 2013/0066293 A1 | 3/2013 | Garfield et al. | |
| 2013/0076030 A1 | 3/2013 | Fog et al. | |
| 2013/0304037 A1* | 11/2013 | Fangrow | A61M 39/1011 604/535 |
| 2014/0052101 A1 | 2/2014 | Stroup | |

FOREIGN PATENT DOCUMENTS

| | | | |
|---|---|---|---|
| EP | 1827568 B1 | 10/2009 | |
| JP | 2001505087 A | 4/2001 | |
| JP | 20088522736 A | 7/2008 | |
| JP | 2010527276 A | 8/2010 | |
| WO | 2006062912 A1 | 6/2006 | |
| WO | 2009052433 A2 | 4/2009 | |
| WO | 2009111596 A2 | 9/2009 | |
| WO | 2009133754 A1 | 11/2009 | |
| WO | 2011139995 A2 | 11/2011 | |
| WO | WO 2015114428 A1 * | 8/2015 | ............ A61M 39/10 |

OTHER PUBLICATIONS

EP11848795 Extended European Search Report dated Mar. 31, 2016.
PCT/US2009/036088 International Search Report and Written Opinion dated Sep. 30, 2009.
PCT/US2011/040583 International Search Report and Written Opinion dated Feb. 23, 2012.
PCT/US2011/064488 International Search Report and Written Opinion dated Jul. 30, 2012.
PCT/US2014/062551 International Search Report and Written Opinion dated Jan. 30, 2015.
JP2013-544659 Office Action dated Nov. 24, 2015.

* cited by examiner

VALVE ASSEMBLY AND METHODS OF USE

CROSS REFERENCE TO RELATED APPLICATIONS

This is a US national phase application under 35 USC § 371 of international patent application No. PCT/US2016/041510, filed 8 Jul. 2016, which itself claims benefit of priority to U.S. provisional patent application 62/190,108, filed 8 Jul. 2015 and U.S. provisional application 62/328,375, filed 27 Apr. 2016; the content of each is herein incorporated by reference in their entirety.

FIELD OF THE INVENTION

The invention relates to devices and methods for controlling the flow of fluid and more specifically to valve assemblies for controlling the in-line flow of fluid, such as controlling the infusion of liquids into patients for medical purposes.

BACKGROUND OF THE INVENTION

A variety of medical treatment and diagnostic procedures require the infusion of fluids, such as the intravenous infusion of medications. Fluids are typically administered through a series of tube-like segments ultimately connecting a reservoir or syringe at one end to a needle inserted into the patient at the opposing end. The segments are typically connected through luer devices, which can be characterized generally as male to female connectors with helical threads.

There are a number of approaches for regulating the flow of fluid through medical tubing. One of the most common is a roller clamp that rolls across tubing in one direction to cutoff flow and in the opposing direction to permit flow. Other approaches have been developed for direct connection to luer devices.

U.S. Pat. No. 8,647,310 by Fangrow Jr. provides a technical approach where a male luer tip and rigid internal member extending into the passageway of the luer tip move relative to one another to open and close the distal most end of the male luer tip. One deficiency of this approach is that it is not applicable to many spike valve connectors since the internal member is rigid and cannot be displaced by the central spike of the spike valve.

U.S. Pat. No. 6,745,998 by Doyle provides at least two alternative approaches for a luer valve. A first approach is configured for connection to a spike valve where a resilient member is elastically displaced from a sealing position against a distal end of a tubular passage using the spike protruding from the spike valve. Once displaced or collapsed, the fluid is permitted to flow through the tubular passage and into the spike valve. A deficiency of this approach is that since opening the valve requires compressing the resilient member, the valve is not applicable to connectors that lack a central spike. In a different approach, a bladder is compressed proximally by a connecting luer (that lacks a spike) to move a forward end of the bladder away from a forward end opening of the tubular member. However, like Fangrow Jr., this approach would not apply to a spike valve because access through the forward end is permitted only after compressing the bladder with the complementary luer.

Accordingly, there remains a need to develop additional valve assemblies for medical applications that can be used with luer connectors that have spike valves and with luer connectors that lack a central spike. There also remains a continued need to ensure valves for medical applications that sealingly connect opposing fluid line connectors prior to valve opening that are easy to operate.

SUMMARY OF THE INVENTION

The invention addresses the above deficiencies in the art and provides related benefits. In one aspect of the invention a valve assembly is provided, which includes an outer housing having a base and an outer shell, which forms a proximal cavity and a distal cavity joined by a canal, wherein base is preferably threaded at a proximal end for luer connection and notched with one or more notches at a distal end; an inner housing configured for longitudinal movement within the distal cavity, the inner housing having one or more through slots aligned to permit access to the one or more notches across the inner housing, and a central boss having a through bore that directs passage of fluid through the inner housing; and a seal positioned within the distal cavity that together with the longitudinal movement of the inner housing regulates the flow of fluid through the valve assembly.

Longitudinal movement of the inner housing distally opens the valve and longitudinal movement of the inner housing proximally closes the valve. Longitudinal movement between the outer shell and inner housing can be by helically turning the inner housing in relation to the outer housing. Helical turning can be by arranging complementary camming elements on the outside surface of the inner housing and on the inside surface of the outer housing.

In some embodiments the inner housing is threaded with connector threads that surround the boss to define a helical axis. Attachment to a fluid line distally is preferably by luer connection with the connector threads. Preferably the connector threads are oriented in a same direction as the camming element on the outside of the inner housing such that rotation of a connecting fluid line in relation to the outer housing sealingly connects the fluid line to the inner housing then continued rotation in a same direction longitudinally moves the inner housing distally to open the valve assembly and thus permit flow. In further embodiments the valve assembly includes a torque limiter mechanism between the outer shell and the inner housing configured to resist the rotational movement of the inner housing until a sufficient radial force is applied, which is designed to occur after sealingly connecting the distal fluid line to the inner housing. This configuration ensures secure connection between a fluid line distally prior to opening the valve. In still further embodiments, the torque limiter mechanism has interengageable formations on the outer shell and the inner housing, the interengageable formations preferably having at least one indent on the inner housing and at least one flexible member on the outer shell biased into engagement in the indent in a closed position, whereby the movement of the inner housing is resisted by engagement of an end face of the indent with the flexible member until the biasing force of the flexible member is overcome. At which time, the inner housing is permitted to helically rotate distally to open the valve assembly.

In some embodiments the one or more through slots of the inner housing are longitudinally adjacent to the one or more notches on the base when the valve is in a closed position. This configuration provides direct access to the notches by traversing the slots with a suitable tool. Direct access permits interaction with the base through the inner housing. In some embodiments, a removable cap is provided, which is configured to reversibly cap the distal cavity. In further embodiments the cap has one or more prongs configured to traverse the one or more through slots to engage the one or more notches so that when capped, rotation of the cap causes rotation of the base, which facilitates attachment to a luer connector to the base.

In some embodiments, the seal is a sealing pin. In some embodiments the sealing pin is deformable but in other embodiments the sealing pin is rigid. In some embodiments the deformable sealing pin bulges radially at a proximal end when compressed. In other embodiments the deformable sealing pin bends about midway between its proximal base and distal tip.

In some embodiments the sealing pin reversibly mates with a distal end of the central boss to regulate the flow of fluid through the valve assembly. In some embodiments the sealing pin reversibly mates with a proximal end of the central boss to regulate the flow of the fluid through the valve assembly. In some embodiments, the sealing pin reversibly mates with the canal to regulate the flow of the fluid through the valve assembly. Reversibly mating can be by way of compression and release of a compressive force.

In related aspect, the invention also provides a valve assembly having an outer housing including a proximal cavity and a distal cavity joined by a canal; an inner housing configured for longitudinal movement within the distal cavity, the inner housing having a central boss having a through bore to direct passage of fluid through the inner housing; a reversibly deformable sealing pin positioned within the central boss, the sealing pin having a proximal base and a distal tip, wherein the sealing pin is configured to deform when applying a sufficient force proximally against the distal tip and substantially reverse deformation upon release of the force, further wherein flow of fluid through the valve assembly is regulated at the proximal base of the sealing pin.

In some embodiments, the outer housing includes a base with one or more notches at a distal end and the inner housing has one or more through slots aligned to permit access to the one or more notches. In some embodiments removable cap is provided, which is configured to reversibly cap the distal cavity, wherein the cap has one or more prongs configured to traverse the one or more through slots to engage the one or more notches so that when capped, rotation of the cap causes rotation of the base.

Longitudinal movement of the inner housing distally opens the valve and longitudinal movement of the inner housing proximally closes the valve. Longitudinal movement between the outer shell and inner housing can be by helically turning the inner housing in relation to the outer housing. Helical turning can be by arranging complementary camming elements on the outside surface of the inner housing and on the inside surface of the outer housing.

In some embodiments the inner housing is threaded with connector threads that surround the central boss to define a helical axis. Attachment to a fluid line distally is preferably by luer connection with the connector threads. Preferably the connector threads are oriented in a same direction as the camming element on the outside of the inner housing such that rotation of a connecting fluid line both connects the fluid line to the inner housing and longitudinally moves the inner housing distally to open the valve assembly and thus permit flow. In further embodiments the valve assembly includes a torque limiter mechanism between the outer shell and the inner housing configured to resist the movement of the inner housing until a sufficient radial force is applied. This configuration ensures secure connection between a fluid line distally prior to opening the valve. In still further embodiments, the torque limiter mechanism has interengageable formations on the outer shell and the inner housing, the interengageable formations preferably having at least one indent on the inner housing and at least one flexible member on the outer shell biased into engagement in the indent in a closed position, whereby the movement of the inner housing is resisted by engagement of an end face of the indent with the flexible member until the biasing force of the flexible member is overcome. At which time, the inner housing is permitted to helically rotate distally to open the valve assembly.

Preferably, the sealing pin is constructed from a flexible or bendable polymer. In some embodiments, the sealing pin is constructed from silicone. In some embodiments the sealing pin is constructed from a polyisoprene.

In some embodiments, the sealing pin is configured to bend about midway between its proximal base and distal tip when sufficient proximal force is applied. In some embodiments, the sealing pin is configured to bulge radially at the proximal base to maintain a fluid tight seal against the central boss or canal.

Preferably, a fluid tight seal is maintained until the longitudinal movement distally of the inner housing. In some embodiments a closed position is characterized as the proximal base of the sealing pin sealed against the central boss and/or the canal. In some embodiments a closed position is maintained when the proximal base of the sealing pin is sealingly mated against the central boss and/or the canal and the sealing pin is displaced from a distal tip of the central boss, such as during deformation. An open position can be defined by the proximal base of the sealing pin spaced apart from both the central boss and the canal.

In another related aspect of the invention a valve assembly is provided having an outer housing including a proximal cavity and a distal cavity joined by a canal; an inner housing configured for longitudinal movement within the distal cavity, the inner housing having a central boss including a through bore to direct passage of fluid through the inner housing; and a seal positioned within the distal cavity that together with the longitudinal movement of the inner housing regulates the flow of fluid through the valve assembly. The outer housing and inner housing also have a torque limiter mechanism, configured to resist the longitudinal movement of the inner housing distally until a sufficient radial force is applied, which is greater than a force required to sealingly connect a luer connector to the inner housing. Preferably, the torque limiter mechanism resists disconnection of the luer connection until after closing the valve.

In another related aspect of the invention a method of attaching a valve assembly to a fluid line is provided, which includes engaging the threads of the base of the valve assembly against a complementary threaded end of a proximal fluid line; and rotating the base by rotation of the cap to continue engagement of the threads until a seal is formed between the fluid line and the valve assembly. In such a method, preferably the valve assembly is characterized as an outer housing having a base and an outer shell, which forms a proximal cavity and a distal cavity joined by a canal, wherein base is threaded at a proximal end and notched with one or more notches at a distal end; an inner housing configured for longitudinal movement within the distal cavity, the inner housing having one or more through slots aligned to permit access to the one or more notches across the inner housing, and a central boss having a through bore that directs passage of fluid through the inner housing; and a seal positioned within the distal cavity that together with the longitudinal movement of the inner housing regulates the flow of fluid through the valve assembly. Still more preferably the assembly the one or more through slots are longitudinally adjacent to the one or more notches when the valve is in a closed position, and further where a removable cap is configured to reversibly cap the distal cavity, wherein the cap comprises one or more prongs configured to traverse the one or more through slots to engage the one or more notches so that when capped, rotation of the cap causes rotation of the base.

In some embodiments, the method also includes removing the cap; mating a distal fluid line to the inner housing; and longitudinally moving the inner housing to permit flow of the fluid through the valve assembly. In still further embodiments, the distal fluid line has a spike valve and the seal is a deformable sealing pin, wherein the step of mating the distal fluid line to the inner housing includes inserting the spike of the spike valve into the central boss thereby displacing the deformable sealing pin away from a distal tip of the central boss while the valve assembly remains closed.

In yet another related aspect, a method of employing a valve assembly is provided, which includes forming a fluid tight seal between the base of the valve assembly and a proximal fluid line; mating a distal fluid line having a spike valve to the inner housing by inserting the spike of the spike valve into the central boss thereby displacing the deformable sealing pin away from a distal tip of the central boss while the valve assembly remains closed. In such a method, preferably the valve assembly is characterized as having an outer housing including a proximal cavity and a distal cavity joined by a canal; an inner housing configured for longitudinal movement within the distal cavity, the inner housing having a central boss having a through bore to direct passage of fluid through the inner housing; a reversibly deformable sealing pin positioned within the central boss, the sealing pin having a proximal base and a distal tip, wherein the sealing pin is configured to deform when applying a sufficient force proximally against the distal tip and substantially reverse deformation upon release of the force, further wherein flow of fluid through the valve assembly is regulated at the proximal base of the sealing pin.

BRIEF DESCRIPTION OF THE DRAWINGS

The invention will be better understood from the following detailed description of preferred embodiments of the invention, taken in conjunction with the accompanying drawings in which like reference numerals refer to like parts and in which.

DETAILED DESCRIPTION OF PREFERRED EMBODIMENTS

As an introduction to the invention and with reference to FIGS. 1-13, the invention includes a valve assembly 10 for regulating the flow of fluid. The valve assembly 10 is particularly useful in the medical field, such as regulating the flow of in-line fluid for infusion of medications in liquid form.

For consistency, the valve assembly 10 is described with reference to a base 102 extending proximate P from an outer shell 104, and regulating fluid that flows distally D through the assembly 10; however, the artisan having ordinary skill in the art to which the invention belongs will recognize that the valve assembly 10 could also regulate fluid flowing in a proximal P direction and therefore is not intended to be limited in regard to the terms the orientation of the base 102 and outer housing 104 or the direction of fluid flowing through the valve assembly 10. That is, whether fluid flows proximally P or distally D, the valve assembly 10 is configured for connection to a first fluid line connector at one end and configured for connection to a second fluid line connector at the opposing end such that the valve assembly 10 regulates the flow of fluid between the two fluid lines in either direction.

Unless defined otherwise, all technical and scientific terms used herein have the same meaning as commonly understood by one of ordinary skill in the art to which this invention belongs. Although methods and materials similar or equivalent to those described herein can be used in the practice or testing of the invention, the preferred methods and materials are now described.

Figure 1:
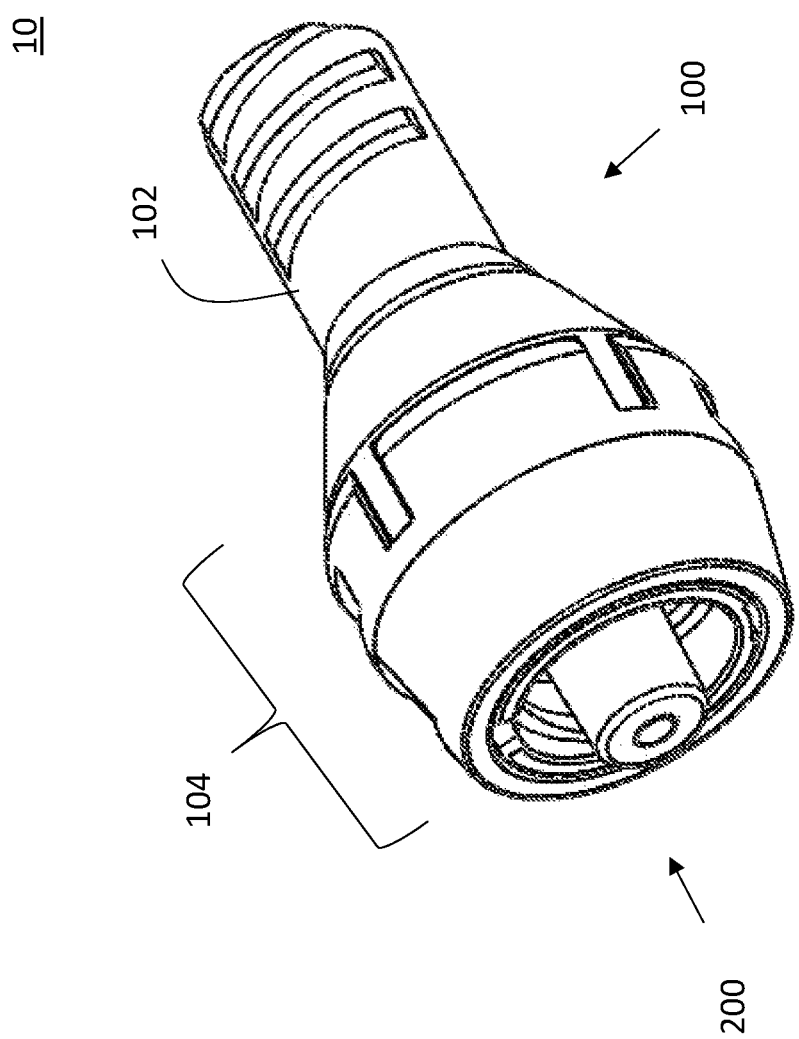
FIG. 1 depicts an exemplary valve assembly 10 in a closed state.
Figure 2:
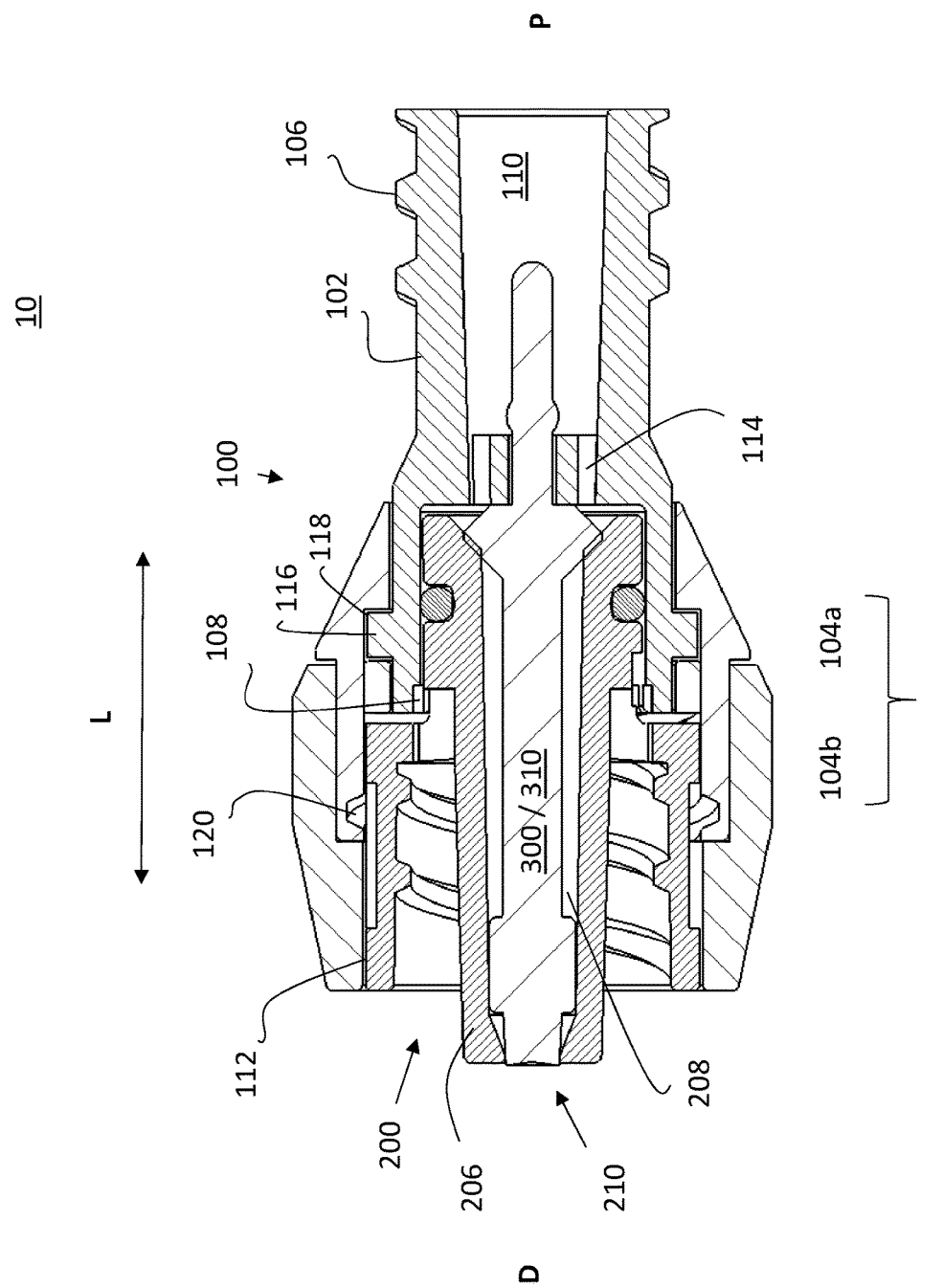
FIG. 2 is cross section of an exemplary valve assembly 10 shown in a closed state.
Figure 3:
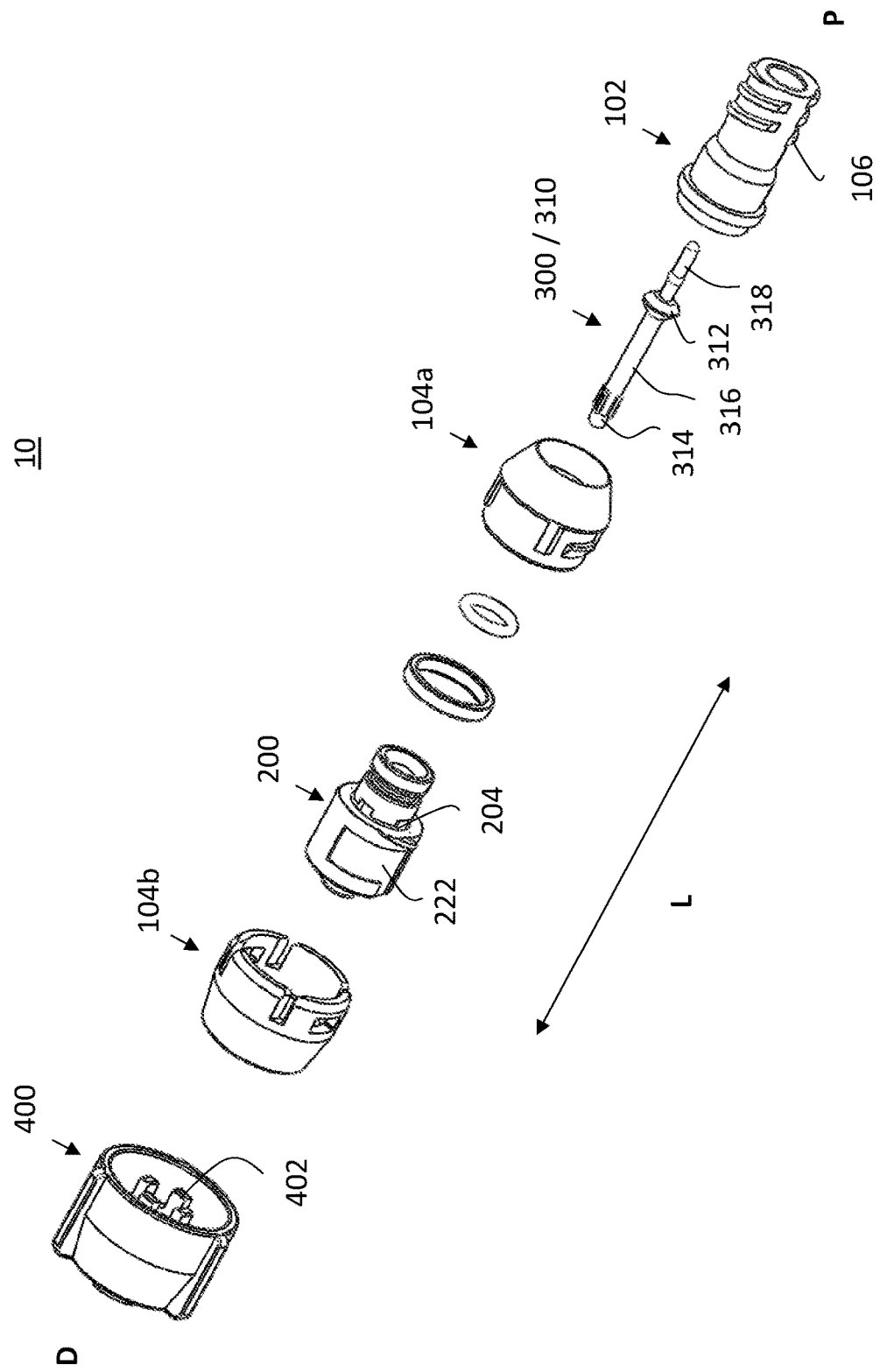
FIG. 3 is an exploded view of an exemplary valve assembly 10.
Figure 4:
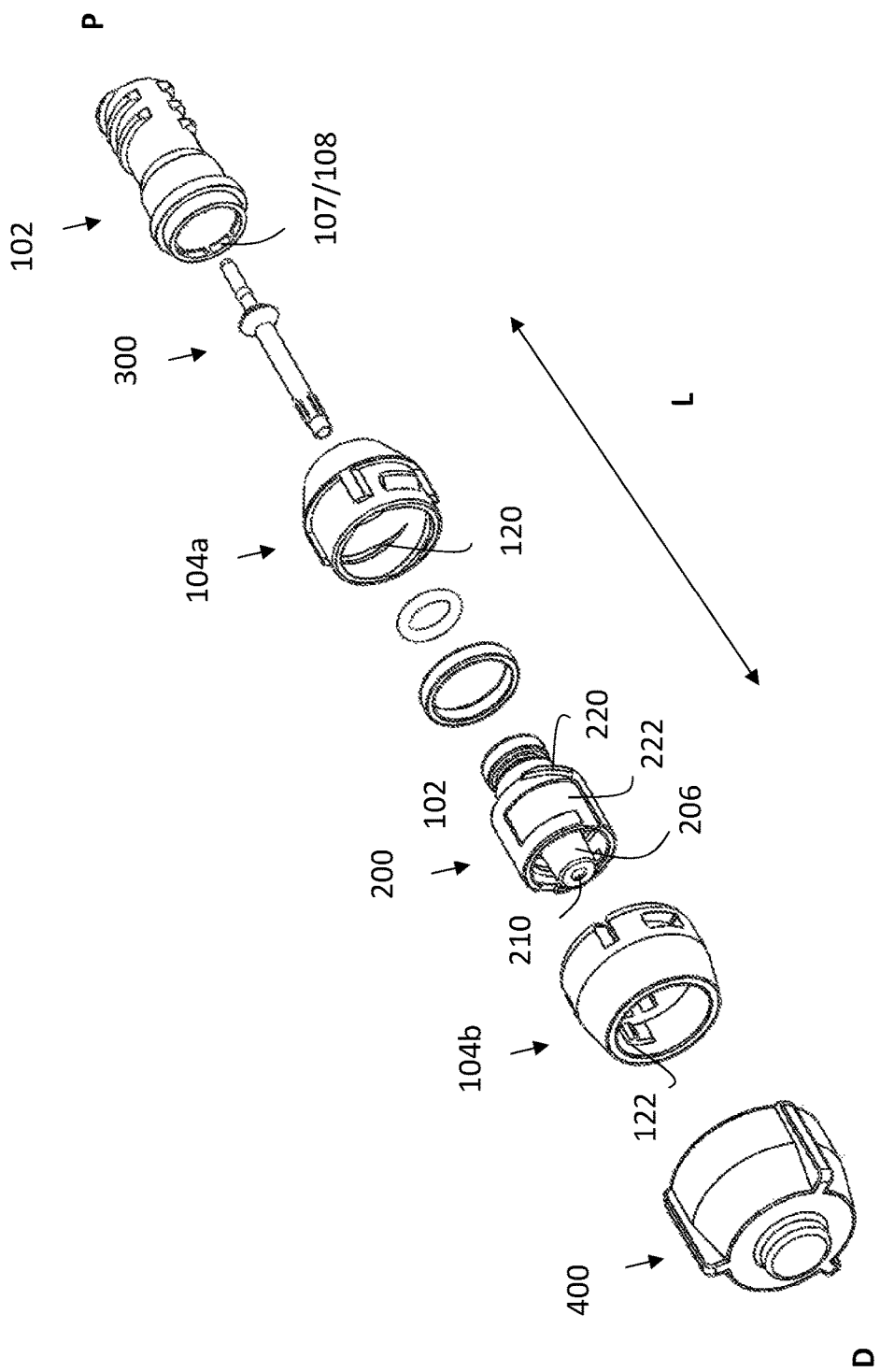
FIG. 4 is an exploded view of the valve assembly 10 of FIG. 3 shown in a different viewing angle.
Figure 5:
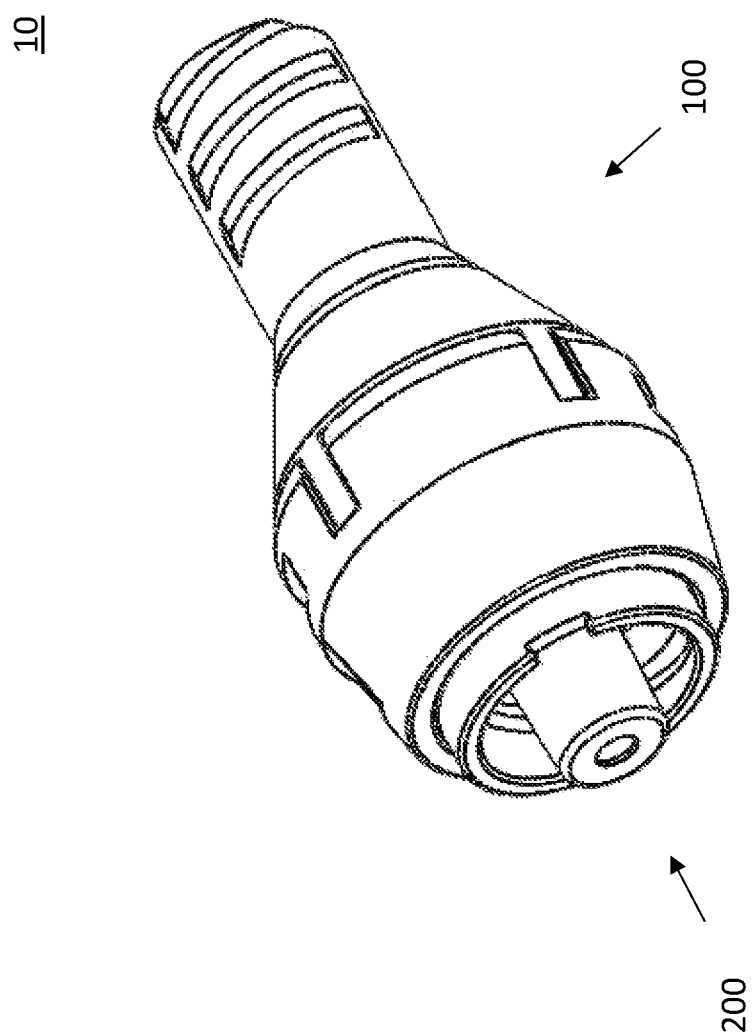
FIG. 5 depicts the valve assembly of FIG. 1 in an open state.
Figure 6:
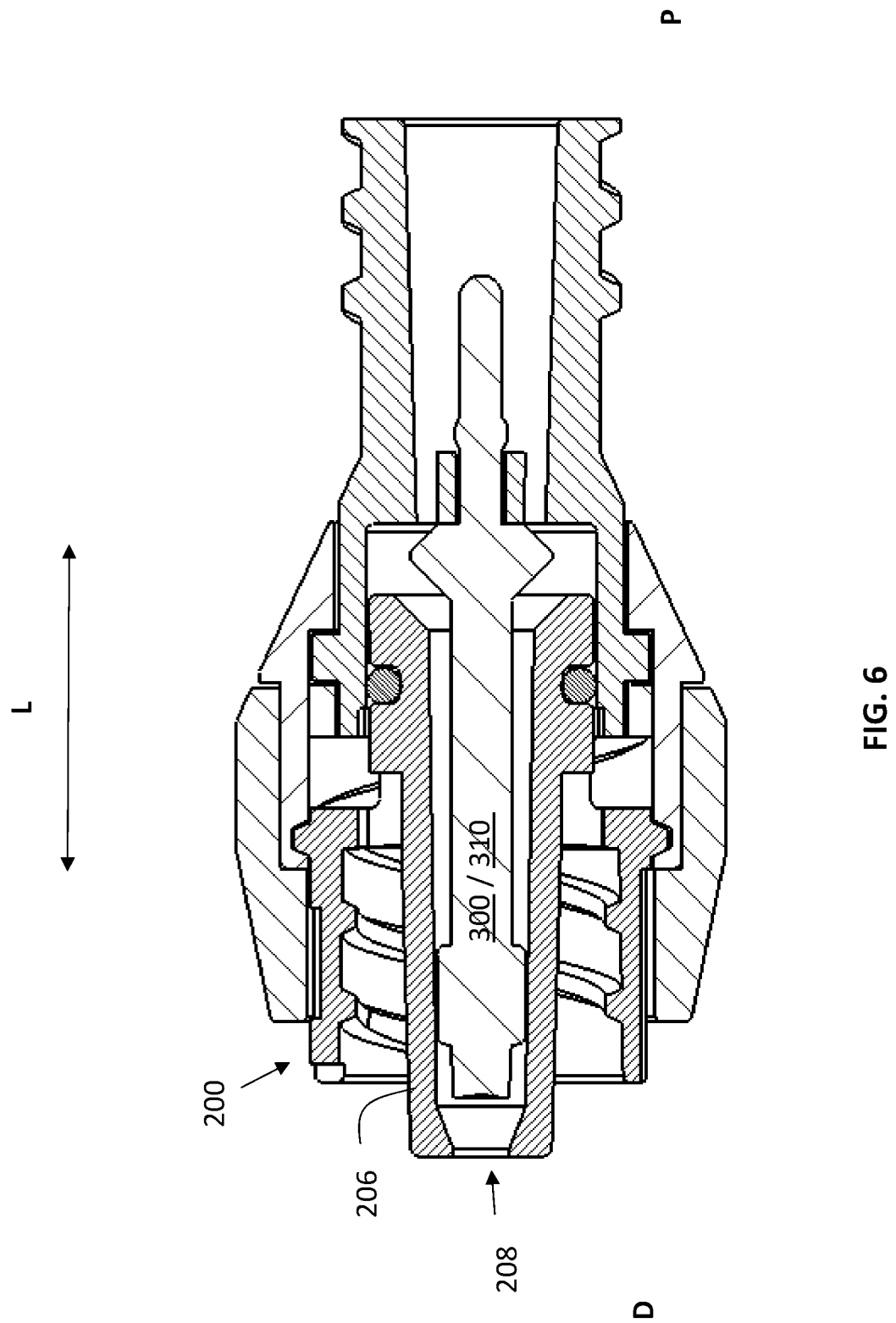
FIG. 6 is a cross section of the valve assembly 10 of FIG. 2 shown in an open state.
Figure 8:
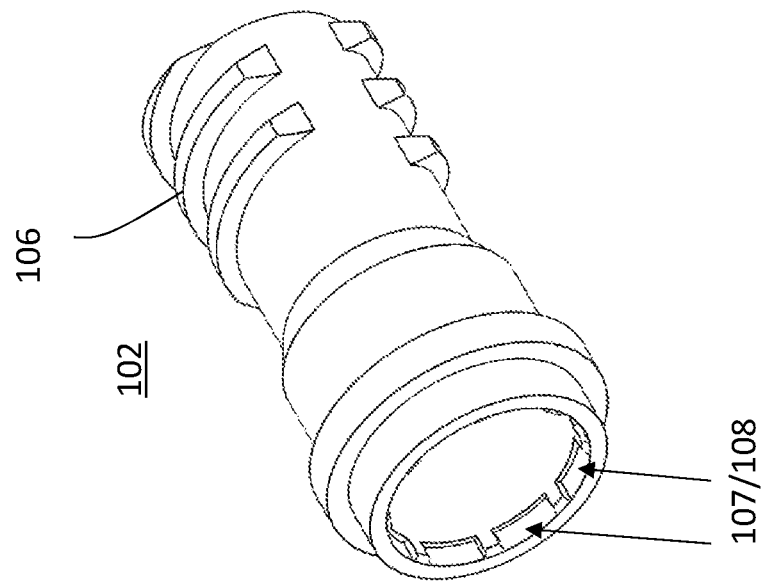
FIG. 8 is an isometric view of an exemplary base 102.
Figure 7:
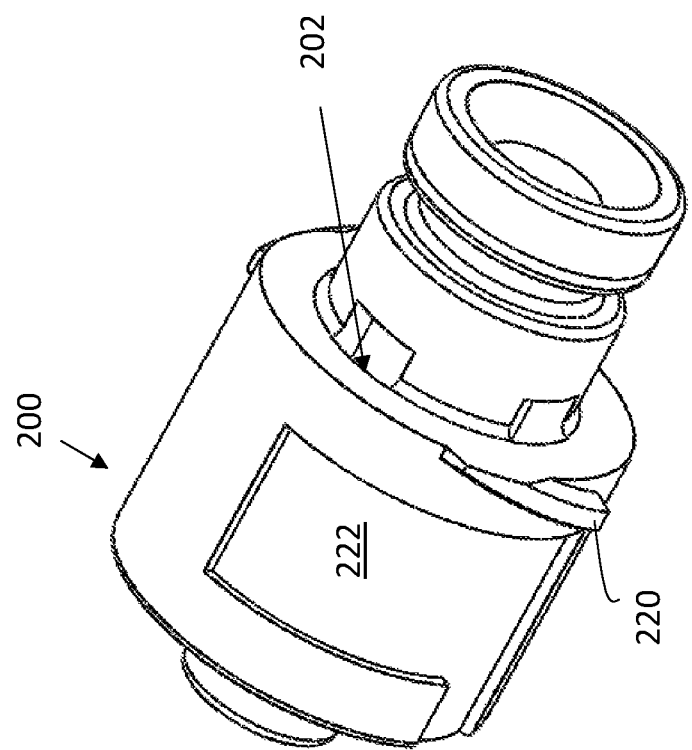
FIG. 7 is an isometric view of an exemplary inner housing 200.
Figure 9:
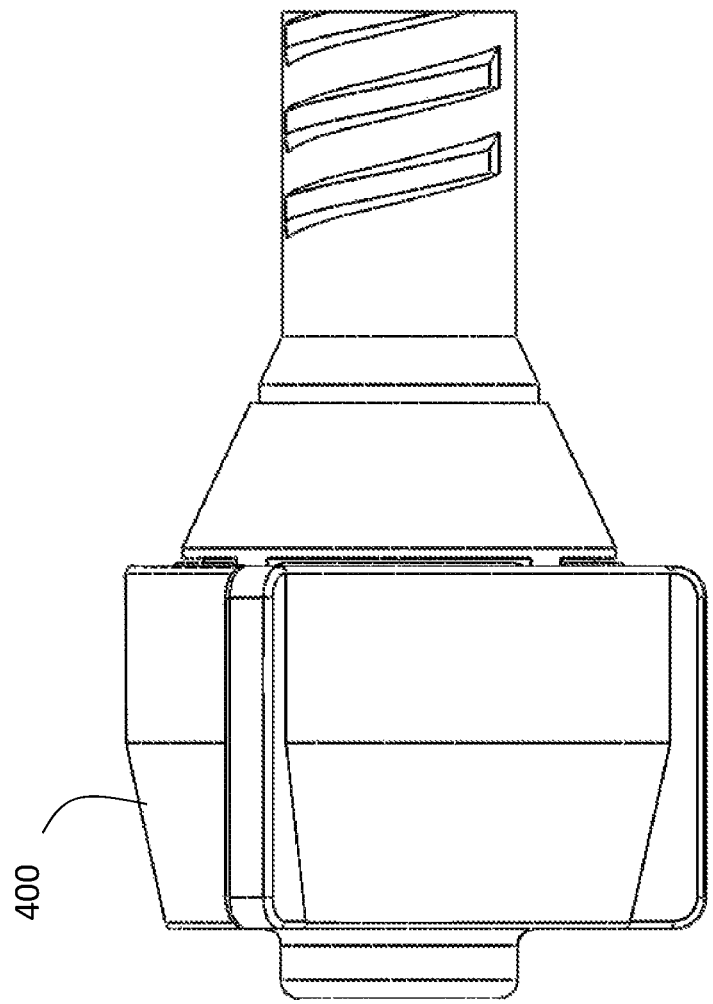
FIG. 9 is depicts an exemplary capped valve assembly 10.
Figure 11:
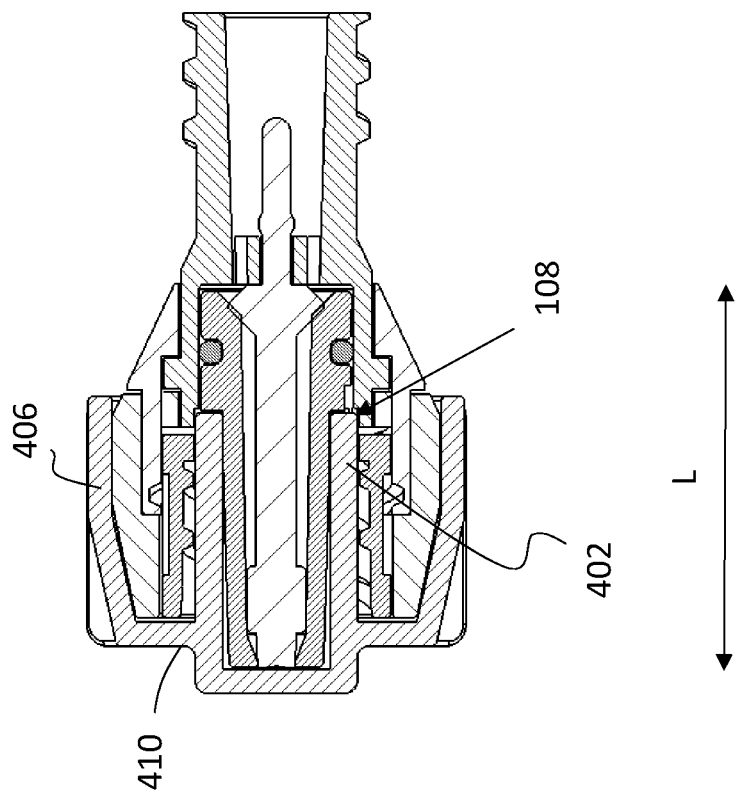
FIG. 11 is a cross section of the capped valve assembly 10 of FIG. 9.
Figure 10:
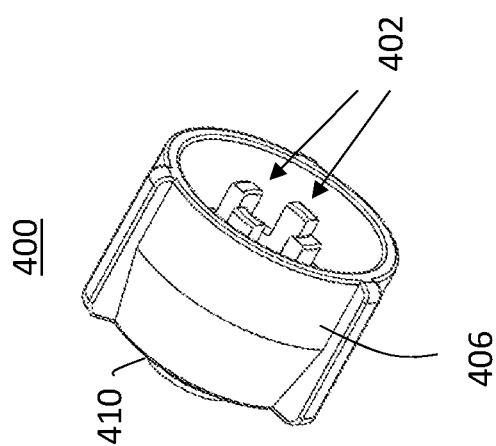
FIG. 10 depicts an exemplary cap 400.

As shown in FIG. 1, the valve assembly 10 has an outer housing 100, which can be defined generally by a base 102 assembled to an outer shell 104. Turning to FIG. 2, the outer shell 104 can be fabricated as a first part 104a and a second part 104b for ease of manufacturing and assembly, but the outer shell 104 has also been formed integrally as a single part.

With reference to FIGS. 1-4, assembly of the outer housing 100 can begin by forming the first part 104a and second part 104b of the outer shell 104 separately, such as by injection molding, then inserting an injection molded base 102 proximally through the first part 104a of the outer shell 104 until locking or snap fitting complementary locking surfaces. The complementary locking surfaces lock the base 102 into position longitudinally L to prevent further longitudinal L sliding. In some embodiments, the base 102 is locked into position longitudinally L but the outer shell 104 is permitted to rotate circumferentially around the base 102 but requiring greater force than that encountered when connecting a distal fluid line and displacing the inner housing 200. In some embodiments the base 102 and outer shell 104 are locked longitudinally L and circumferentially. In some embodiments a protruding ring 116 encircling the base 102 snap fits into a circular recess 118 along the inner surface of the outer shell 104. After which, the second part 104b of the outer shell 104 can be friction fit or snap fit over the first part 104a of the outer shell 104. Once assembled, the outer housing 100 forms a proximal cavity 110 fluidly coupled to a distal cavity 112 by a canal 114, thereby providing a path for passing fluid, preferably a liquid, such as a medication for infusion into a patient.

The base 102 is configured for connection to a proximal fluid line preferably using luer connection via threads 106 that complement threads on a luer connector. At the opposing end of the base 102 is a receiving member 107, which can be embodied as a female structure for receiving a complementary male structure, but is preferably is embodied as one or more notches 108 notched from the base 102. The notches 108 could be positioned along the outside surface of the base 102 but are preferably positioned circumferentially along an inner surface of the base 102. Notches can also be provided on the inner housing 200 that align with the notches 108 during assembly. When embodied as notches 108, there can be one notch 108, two notches 108, three notches 108, four notches 108 or more than four notches 108 spaced regularly or irregularly around the inner or outer surface of the base 102. Preferably there are at least four notches 108.

With reference to FIGS. 1-6, an inner housing 200 is positioned within the distal cavity 112 and configured for longitudinal L movement, which together with the seal 300 regulates the flow of fluid through the valve assembly 10. Longitudinal L movement can be by way of helically arranged complementary camming elements 120, 220 between the outer shell 104 and the inner housing 200. This permits longitudinal L movement by helically turning the inner housing 200 in relation to the outer shell 104 or helically turning the outer shell 104 in relation to the inner housing 200. Operationally, once the distal fluid line is sealingly connected, continued rotation of the distal fluid line luer in relation to the outer housing 100 extends the inner housing 200 distally in relation to the outer housing 100 thereby opening the valve assembly 10 to permit fluid flow. Relatedly, reversing rotation would retract the inner housing 200 proximally thereby closing the valve assembly 10 to prevent fluid flow.

Differentiating between rotational connection of the distal fluid line and longitudinal displacement of the inner housing 200 was a challenge that had to be overcome. It is important that the distal fluid line be sealingly connected prior to opening the valve 10, and rotation of the distal fluid line be in a same direction for both distal fluid line connection and valve 10 opening. Similarly, it is important to close the valve 10 before disconnecting the distal fluid line. The solution was the formation of a torque limiter mechanism 122, 222 between the outer shell 104 and the inner housing 200. When the valve assembly 10 is in a closed orientation, the torque limiter mechanism 122, 222 resists rotation of the inner housing 200 relative to the outer housing 100 until a sufficient force is applied. By defining this sufficient force to be greater than the rotational force applied for connecting a distal fluid line to the inner housing 200, the valve assembly 10 ensures the distal fluid line is securely connected prior to opening the valve assembly 10. Once the sufficient force is applied, the torque limiter 122, 222 releases to permit the helical rotation of the inner housing 200 in relation to the outer housing 100 thereby opening the valve assembly 10. Similarly, by defining the force required for helical rotation after release of the torque limiter 122, 222 to be less than that of disconnecting the distal fluid line from the valve assembly 10, continued rotation in the opposite direction of an open valve assembly 10 first closes the valve assembly 10 then disconnects the distal fluid line from the inner housing 200. Structurally, the torque limiter mechanism 122, 222 preferably includes interengageable formations on the outer shell 104 and inner housing 200. Most preferably the interengageable formations include at least one indent 222 on the inner housing 200 and at least one flexible member 122 on the outer shell 104 biased into engagement in the indent 222 when the valve is in the closed position. In such a configuration movement of the inner housing 200 is initially resisted during connection with the distal line by engagement of an end face 224 of the indent 222 with the flexible member 122 until the biasing force of the flexible member 122 is overcome. Once overcome, continued rotational force rotates the inner housing 200 in relation to the outer shell 104, which longitudinally L displaces the inner housing 200 distally thereby opening a closed valve assembly 10. Though less preferred, the torque limiter mechanism 122, 222 could also be embodied as two opposing flexible members on the outer housing 100 and inner housing 200 based together until a biasing force is overcome.

In further embodiments, the interengageable formations include diametrically opposite first and second indents 222 on the inner housing 200 and diametrically opposed flexible members 122 on the outer shell 104, which engage the respective indents 222 in a closed position. In such an embodiment, the valve assembly 10 is preferably open with less than a 180 degree turn of the inner housing 200 in relation to the outer shell 104.

With reference to FIGS. 2-9, preferably, the inner housing 200 has one or more through slots 202 permitting access to the receiving member 107 of the base 102 through the inner housing 200. In some embodiments there are two through slots 202. In other embodiments there are three through slots 202. In other embodiments there are four through slots 202. In still other embodiments there are more than four through slots 202. In some embodiments, there are more through slots 202 than notches 108. Preferably, at least one of the one or more through slots 202 are longitudinally L aligned and adjacent to one of the one or more notches 108 to permit linear access to the notches 108 across the inner housing 200 when the valve 10 is in a closed position.

With reference to FIGS. 1-11, preferably, the valve assembly 10 is provided with a tool to traverse the through slots 202 and engage the receiving member 107 (or notches 108) to directly rotate the base 102. In preferred embodiments, the tool is in the form of a removable cap 400 that reversibly caps the distal cavity 112, thereby decreasing direct handling of the distal D end of the inner housing 200 when connecting the base 102 to a proximal fluid line. In an exemplary embodiment the cap 400 has one or more prongs 402 configured to fit through the one or more slots 202 and rest within the one or more notches 108 so that rotation of the cap 400 directly rotates the base 102.

The valve assembly 10 can be easily connected at each end and operated. Proximal P connection to a fluid line connector is conveniently accomplished by rotation of the cap 400, with its prongs 402 received by or engaged in the notches 108. Direct engagement between the prongs 402 and the notches 108 permit turning the base 102 via the cap 400. Connecting to a fluid line distally D can be accomplished by removing the cap 400 and rotating of the outer shell 104, which also rotates the inner housing 200 due to the torque limiter mechanism 122, 222, or by rotating the fluid line in relation to the inner housing 102. Once connected, longitudinal L displacement of the inner housing 200 can be by continued rotation of the outer shell 104 or the sealed distal fluid line in relation to one another. Helical movement longitudinally L displaces the inner housing 200 distally, which opens the valve assembly 10; and helical movement in the opposite direction of an open valve assembly 10 proximally returns the inner housing 200 and thus closes the valve assembly 10. Continued rotation disconnects the fluid line.

Longitudinal L displacement of the inner housing 200 regulates the flow of fluid through interaction with the seal 300, which is preferably embodied with an elongated longitudinal extent 316 and a proximal base 312 (also referred to as a "sealing pin 310"), optionally with a proximal extension 318 for attachment to the base 102 of the outer shell 100. In particular, longitudinal L movement of the inner housing 200 distally D moves the central boss 206 away from the seal 300, which opens the valve assembly 10, and longitudinal L movement of the inner housing 200 proximally P moves the central boss 206 towards and against the seal 300 to close the valve assembly 10. The seal 300 can operate using different modes.

In some embodiments, flow of fluid is regulated through interfering with the distal end of the canal 114, which joins the proximal cavity 110 and the distal cavity 112. This can be accomplished by compressing the seal 300 with the inner housing 200 against the canal 114 in a closed state and releasing the compressive force to permit displacement of the seal 300 from the canal 114 in an open state. In some embodiments (not shown) the seal 300, in particular the proximal base 312 of the seal 300 bulges radially when compressed to form a fluid tight seal at the canal 114 and retreats when decompressed to permit passage of fluid into the distal cavity 110. In such embodiments, the seal is deformable at its base 312 and may be deformable or rigid along its longitudinal extent 316 (shown in FIGS. 12-13).

In other embodiments, the base 312 of the seal 300 is shaped complementary to the proximal end of the central boss 206 such that the seal 300 reversibly mates against the central boss 206 to seal fluid tight when the valve 10 is closed and moves away from the fluid tight mating when the valve 10 is open. In this configuration the seal 300 can be deformable or rigid along its longitudinal extent 316, but is preferably deformable (shown in FIGS. 12-13).

Figure 12:
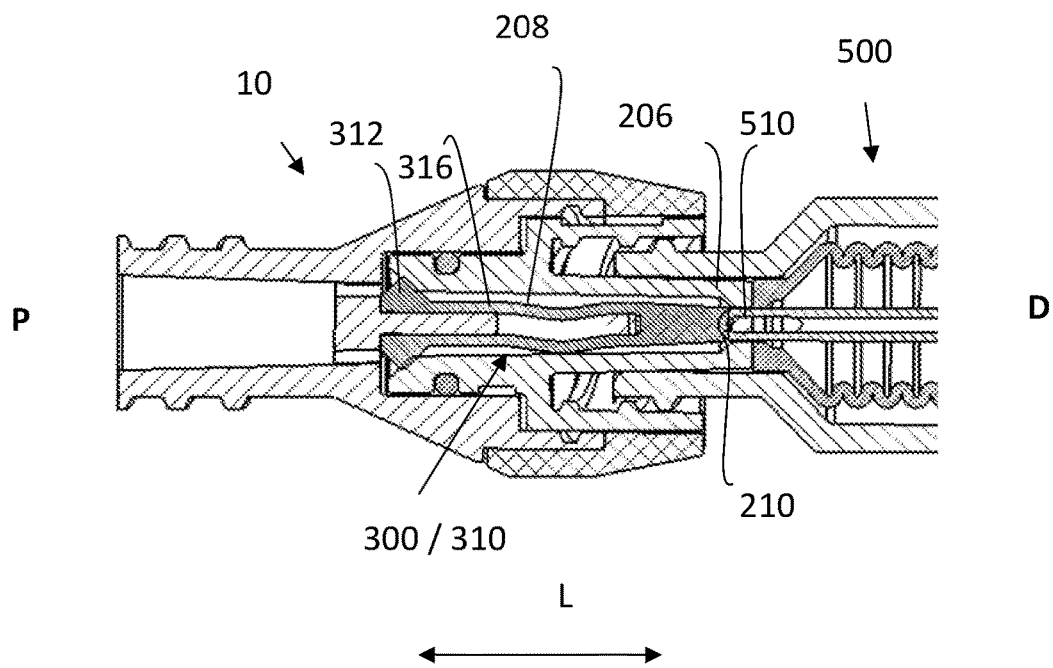
FIG. 12 depicts an exemplary valve assembly 10 in a closed state with a mated spike valve 500 and FIG. 13 depicts the valve assembly 10 of FIG. 12 in an open state with a mated spike valve 500.
Figure 13:
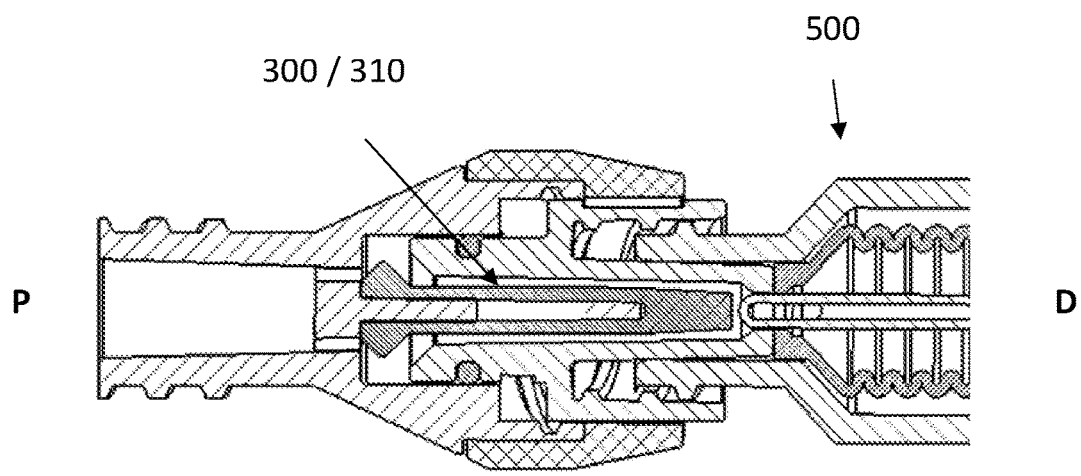

As shown more clearly in FIGS. 12-13, in some embodiments, the seal 300 reversibly deforms along its longitudinal extent 316. This configuration may be preferred when connecting the valve assembly 10 distally to a spike valve 500. In this configuration, a deformable sealing pin 310 extending into the through bore 208 of the central boss 206 is configured to bend and flex away from the distal aperture 210 of the boss 206 to ensure proper seating of a spike 510 into the central boss 206. An implication of this configuration is that the sealing pin 310 is displaced from the distal aperture 210 of the boss 206 while the valve 10 remains closed. As such, the distal end of the central boss 206 would not itself prevent flow of fluid through the valve 10.

Providing a configuration where the sealing pin 310 bends away from the distal aperture 210 of the central boss 206 while the valve assembly 10 remains closed provides a number of benefits. For instance, a deformable sealing pin 310 that bends along its longitudinal extent 316 permits the valve assembly 10 to be used with both spike connectors 500 and connectors that lack a spike 510. In addition it also permits the valve assembly 10 to be used with a number of different sized spikes 510. In particular, spike valves 500 having different sized spikes 510 can be properly seated prior to opening the valve assembly 10. In addition, a deformable sealing pin 310 that bends along its longitudinal extent ensures proper mating of the central boss 206 and spike 510 prior to opening the valve assembly 10 by providing a suitable guided path.

FIGS. 12-13 also depict the delayed opening of the valve assembly 10 when connecting the valve assembly 10 distally to a spike valve 500. As shown in FIG. 12, initial rotation of a central spike valve 500 relative to the valve assembly 10 causes longitudinal L movement and mating of the central spike 510 of the spike valve 500 against the deformable sealing pin 310 within the central boss 206. Continued rotation increases the force longitudinally L against the deformable sealing pin 310, which causes the deformable sealing pin 310 to bend such that the sealing pin 310 is displaced away from the distal aperture 210 of the central boss 206 to permit entry of the central spike 510 into the boss 206. Since release of the in-line fluid is regulated in a region of the proximal end of the central boss 206 and sealing pin 310, which remains sealed during insertion of the central spike 510, bending and thus displacement of the sealing pin 310 away from the distal aperture 210 of the central boss 206 does not cause the in-line fluid to flow through the valve 10. In this configuration the valve 10 remains closed even though the sealing pin 310 is displaced from the distal aperture of the boss 206. Once the central spike 510 is maximally inserted into the central boss 206 and the sealing pin 310 is fully displaced from the distal aperture 210 of the central boss 206 continued rotation of the spike valve 500 moves the central boss 206 distally together with the central spike valve 500, thereby unsealing the valve 10 at the proximal end of the central boss 206 and base 312 of the sealing pin 310. Flow of in-line fluid is then permitted across the central boss 206 and into the spike valve 500.

In still another embodiment, the flow of fluid through valve assembly 10 is regulated at least in part by reversibly maintaining the sealing pin 310 with a distal end of the through bore 208 of the central boss 206. In this approach, the sealing pin 310 is preferably rigid or substantially rigid and the distal fluid line lacks a spike 510 connector.

Returning to FIGS. 3-4 and FIGS. 9-11, the invention also provides a cap 400 sized to cover the distal cavity 112 of the valve assembly 10. The cap 400 is defined generally by a top 404 joined to a circular sidewall 406. The sidewall 406 preferably has a flat inner surface free of threads so that it is friction fit against the outer housing 100. The cap 400 has one or more prongs 402 configured to traverse the through slots 204 of the inner housing 200 for engagement against the receiving member 107. More preferably, the one or more prongs 402 include more than one prong 402. In some embodiments, the cap 400 has two prongs 402. In other embodiments the cap 400 has three prongs 402. In other embodiments, the cap 400 has four prongs 402. In other embodiments, the cap 400 has five prongs 402. In other embodiments, the cap 400 has six prongs 402. In other embodiments, the cap 400 has more than six prongs 402. In some embodiments, the cap 400 has fewer prongs 402 than there slots 202. In some embodiments the prongs 402 are in a circular arrangement and extend longitudinally L from the top 404.

With reference to FIGS. 1-13, a valve assembly 10 for controlling fluid flow along a fluid line is also provided, which includes an outer housing 100 having a proximal cavity 110 and a distal cavity 112 joined by a canal 114; an inner housing 200 configured for longitudinal L movement within the distal cavity 112, the inner housing 200 having a central boss 206 comprising a through bore 208 to direct passage of fluid through the inner housing 200; and a seal 300 positioned within the distal cavity 112 that together with the longitudinal L movement of the inner housing 200 regulates the flow of fluid through the valve assembly 10; wherein the outer housing 100 and inner housing 200 comprise a torque limiter mechanism 122, 222 configured to resist the longitudinal movement of the inner housing 200 distally until a sufficient radial force is applied, which is greater than a force required to sealingly connect a luer connector to the inner housing 200. Preferably, the torque limiter mechanism 122, 222 resists disconnection of the luer connection until after closing the valve 10. Most preferably, the torque limiter mechanism 122, 222 includes interengageable formations on the outer shell 104 and the inner housing 200, the interengageable formations having at least one indent 222 on the inner housing 200 and at least one flexible member 122 on the outer shell 104 biased into engagement in the indent 222 in a closed position, whereby the movement of the inner housing 200 is resisted by engagement of an end face 224 of the indent 222 with the flexible member 122 until the biasing force of the flexible member 122 is overcome.

The invention also provides a method of attaching a valve assembly 10 to a fluid line. An exemplary valve assembly includes an outer housing 100 having a base 102 and an outer shell 104, which forms a proximal cavity 110 and a distal cavity 112 joined by a canal 114, wherein the base 102 is threaded 106 at a proximal end and notched with one or more notches 108 at a distal end; an inner housing 200 configured for longitudinal L movement within the distal cavity 112, the inner housing 200 having one or more through slots 204 aligned to permit access to the one or more notches 108 across the inner housing 200, and a central boss 206 having a through bore 208 that directs passage of fluid through the inner housing 200; and a seal 300 positioned within the distal cavity 112 that together with the longitudinal L movement of the inner housing 200 regulates the flow of fluid through the valve assembly 10. In further embodiments the one or more through slots 202 of the inner housing 200 are longitudinally L adjacent to the one or more notches 108 on the base 102 when the valve 10 is in a closed position. This configuration provides direct access to the notches 108 by traversing the slots 202 with a suitable tool. Direct access permits interaction with the base 102 through the inner housing 200. In some embodiments, a removable cap 400 is provided, which is configured to reversibly cap the distal cavity 112. In further embodiments the cap 400 has one or more prongs 402 configured to traverse the one or more through slots 202 to engage the one or more notches 108 so that when capped, rotation of the cap 400 causes rotation of the base 102.

In some embodiments, the method includes engaging the threads 106 of the base 102 of the valve assembly 10 against a complementary threaded end of a proximal fluid line, such as through a luer connector; and rotating the base 102 by rotation of the cap 400 to continue engagement of the threads 106 until a seal is formed between the fluid line and the valve assembly 10.

In some embodiments the method further includes removing the cap 400; mating a distal fluid line to the inner housing 200; and longitudinally L moving the inner housing 200 to permit flow of the fluid through the valve assembly 10.

In some embodiments the distal fluid line includes a spike valve 500 and the seal 300 is a deformable sealing pin 310, wherein the step of mating the distal fluid line to the inner housing 200 includes inserting the spike 510 of the spike valve 500 into the central boss 206 thereby displacing the deformable sealing pin 310 away from a distal tip 314 of the central boss 206 while the valve assembly 10 remains closed.

In related method, the invention also includes a method of employing a valve assembly 10, where the valve assembly 10 includes an outer housing 100 including a proximal cavity 110 and a distal cavity 112 joined by a canal 114; an inner housing 200 configured for longitudinal L movement within the distal cavity 112, the inner housing 200 having a central boss 206 having a through bore 208 to direct passage of fluid through the inner housing 200; a reversibly deformable sealing pin 310 positioned within the central boss 206, the sealing pin 310 having a proximal base 312 and a distal tip 314, wherein the sealing pin 310 is configured to deform when applying a sufficient force proximally against the distal tip 316 and substantially reverse deformation upon release of the force, further wherein flow of fluid through the valve assembly 10 is regulated at the proximal base 312 of the sealing pin 310.

In some embodiments the method includes forming a fluid tight seal between the base 102 of the valve assembly 10 and a proximal fluid line; mating a distal fluid line having a spike valve 500 to the inner housing 200 by inserting the spike 510 of the spike valve 500 into the central boss 206 thereby displacing the deformable sealing pin 310 away from a distal tip 314 of the central boss 206 while the valve assembly 10 remains closed; and longitudinally L moving the inner housing 200 to permit flow of the fluid through the valve assembly 10.

The foregoing disclosure of exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

REFERENCE LISTING

Distal D
Proximal P
Longitudinal L
Valve assembly 10
Outer housing 100
Base 102
Outer shell 104
First part 104a
Second part 104b
Base threads 106
Receiving member 107
Notch 108
Proximal cavity 110
Distal cavity 112
Canal 114

Ring 116
Recess 118
Camming element 120
Flexible member of a torque limiter mechanism 122
Inner housing 200
Slot 202
Connector threads 204
Central boss 206
Through bore 208
Distal tip/aperture 210
Connector threads 210
Camming element 220
Indent 222
End face 224
Seal 300
Sealing pin 310
Proximal base 312
Distal tip 314
Longitudinal extent 316
Proximal Extension 318
Cap 400
Prong 402
Spike valve 500
Spike 510

What is claimed is:

1. A valve assembly comprising:
an outer housing comprising a base and an outer shell, which forms a proximal cavity and a distal cavity joined by a canal, wherein the base is threaded at a proximal end and notched with one or more recessed notches at a distal end;
an inner housing configured for longitudinal movement within the distal cavity, the inner housing comprising one or more through slots longitudinally aligned with the one or more recessed notches to permit linear access to the one or more recessed notches through the one or more through slots of the inner housing, and a central boss comprising a through bore that directs passage of fluid through the inner housing; and
a seal positioned within the distal cavity that together with the longitudinal movement of the inner housing regulates the passage of fluid through the valve assembly, wherein the seal is a sealing pin that reversibly mates with a distal aperture of the central boss to regulate the passage of fluid through the valve assembly.

2. The valve assembly according to claim 1, wherein the outer shell and inner housing comprise complementary camming elements, wherein the longitudinal movement occurs by helically turning the inner housing in relation to the outer housing.

3. The valve assembly according to claim 1, wherein the inner housing comprises connector threads that surround the boss to define a helical axis.

4. The valve assembly according to claim 1, wherein the sealing pin is deformable.

5. The valve assembly according to claim 4, wherein the sealing pin is configured to bulge radially at a base when compressed.

6. The valve assembly according to claim 1, wherein the sealing pin is rigid.

7. The valve assembly according to claim 1, further comprising a torque limiter mechanism between the outer shell and the inner housing configured to resist the movement of the inner housing distally until a sufficient radial force is applied.

8. The valve assembly according to claim 7, wherein the torque limiter mechanism comprises interengageable formations on the outer shell and the inner housing, the interengageable formations comprising at least one indent on the inner housing and at least one flexible member on the outer shell biased into engagement in the indent in a closed position, whereby the movement of the inner housing is resisted by engagement of an end face of the indent with the flexible member until the biasing force of the flexible member is overcome.

9. The valve assembly according to claim 1, wherein distal movement of the central boss is configured to open the valve assembly.

10. The valve assembly according to claim 1, wherein the one or more through slots are longitudinally adjacent to the one or more recessed notches when the valve is in a closed position.

11. The valve assembly according to claim 10, further comprising a removable cap configured to reversibly cap the distal cavity, wherein the cap comprises one or more prongs configured to linearly traverse the one or more through slots to engage the one or more recessed notches so that when capped, rotation of the cap causes rotation of the base.

12. A method of employing a valve assembly within a fluid line, comprising:
engaging the threads of the base of the valve assembly according to claim 11 against a complementary threaded end of a proximal fluid line; and
rotating the base by rotation of the cap to continue engagement of the threads until a seal is formed between the fluid line and the valve assembly.

13. The method according to claim 12, further comprising:
removing the cap;
mating a distal fluid line to the inner housing; and
longitudinally moving the inner housing distally to permit passage of the fluid through the valve assembly.

14. The method according to claim 13, wherein the distal fluid line comprises a spike valve and the seal comprises a deformable sealing pin, wherein the step of mating the distal fluid line to the inner housing comprises inserting the spike of the spike valve into the central boss thereby displacing the deformable sealing pin away from a distal tip of the central boss while the valve assembly remains closed.

15. A valve assembly comprising:
an outer housing comprising a proximal cavity, a base with one or more notches at a distal end, and a distal cavity joined to the base by a canal;
an inner housing configured for longitudinal movement within the distal cavity, the inner housing comprising one or more through slots aligned to permit access to the one or more notches, and a central boss comprising a through bore to direct passage of fluid through the inner housing, wherein movement of the central boss distally is configured to open the valve assembly;
a reversibly deformable sealing pin positioned within the central boss, the sealing pin comprising a proximal base and a distal tip, wherein the sealing pin is configured to deform when applying a sufficient force proximally against the distal tip and substantially reverse deformation upon release of the force by movement of the central boss distally, further wherein flow of fluid through the valve assembly is regulated at the proximal base of the sealing pin; and
a removable cap configured to reversibly cap the distal cavity, wherein the cap comprises one or more prongs configured to traverse the one or more through slots to engage the one or more notches so that when capped, rotation of the cap causes rotation of the base.

16. The valve assembly according to claim 15, wherein the one or more notches are recessed notches.

17. A valve assembly comprising:
an outer housing comprising a proximal cavity and a distal cavity joined by a canal;
an inner housing configured for longitudinal movement within the distal cavity, the inner housing comprising a central boss comprising a through bore to direct passage of fluid through the inner housing, further wherein movement of the central boss distally is configured to open the valve assembly; and
a reversibly deformable sealing pin positioned within the central boss, the sealing pin comprising a proximal base and a distal tip, wherein the sealing pin is configured to deform when applying a sufficient force proximally against the distal tip and substantially reverse deformation upon release of the force, further wherein flow of fluid through the valve assembly is regulated at the proximal base of the sealing pin;
wherein an open position is defined by the proximal base of the sealing pin spaced apart from both the central boss and the canal.

18. A method of employing a valve assembly within a fluid line, comprising:
forming a fluid tight seal between a base of the valve assembly according to claim 17 and a proximal fluid line;
mating a distal fluid line comprising a spike valve to the inner housing by inserting the spike of the spike valve into the central boss thereby displacing the deformable sealing pin away from a distal aperture of the central boss while the valve assembly remains closed; and
longitudinally moving the inner housing distally to permit flow of the fluid through the valve assembly.

19. A valve assembly comprising:
an outer housing comprising a base and an outer shell, which forms a proximal cavity and a distal cavity joined by a canal, wherein the base is threaded at a proximal end and notched with one or more notches at a distal end;
an inner housing configured for longitudinal movement within the distal cavity, wherein the longitudinal movement of the inner housing distally is configured to open the valve assembly, the inner housing comprising one or more through slots longitudinally aligned to permit linear access to the one or more notches through the one or more through slots of the inner housing, and a central boss comprising a through bore that directs passage of fluid through the inner housing;
a seal positioned within the distal cavity that together with the longitudinal movement of the inner housing regulates the passage of fluid through the valve assembly; and
a removable cap configured to reversibly cap the distal cavity, wherein the cap comprises one or more prongs configured to linearly traverse the one or more through slots to engage the one or more notches so that when capped, rotation of the cap causes rotation of the base.

20. The valve assembly according to claim 19, wherein the longitudinal movement is also rotational.

* * * * *